(12) United States Patent
Whitney

(10) Patent No.: US 6,211,254 B1
(45) Date of Patent: Apr. 3, 2001

(54) PROCESS FOR RECYCLING HETEROGENEOUS WASTE

(76) Inventor: John P. Whitney, 537 Vulcan Rd., Haskell, AR (US) 72015

( * ) Notice: Subject to any disclaimer, the term of this patent is extended or adjusted under 35 U.S.C. 154(b) by 0 days.

(21) Appl. No.: 09/326,982

(22) Filed: Jun. 7, 1999

(51) Int. Cl.[7] .............................. C07C 27/00; C07C 1/00; C07C 1/02; C10J 1/28; C01C 1/00
(52) U.S. Cl. ...................... 518/704; 48/197 R; 585/240; 252/373; 423/352
(58) Field of Search ...................... 518/702, 703, 518/704, 700; 48/197 R; 585/240; 252/373; 423/352

(56) References Cited

U.S. PATENT DOCUMENTS

| | | | |
|---|---|---|---|
| 4,497,637 | 2/1985 | Purdy et al. . | |
| 4,572,829 | 2/1986 | Fuderer | 423/359 |
| 4,628,066 | 12/1986 | Bonnell et al. | 518/700 |
| 4,631,183 | 12/1986 | Lalancette et al. | 423/659 |
| 4,725,380 | 2/1988 | Plato | 252/376 |
| 4,766,154 | 8/1988 | Bonnell et al. | 518/700 |
| 4,801,574 | 1/1989 | Brown et al. | 502/342 |
| 4,829,039 | 5/1989 | White et al. | 502/152 |
| 4,869,731 | 9/1989 | Schulz | 48/197 R |
| 4,910,227 | 3/1990 | Brown et al. | 518/700 |
| 4,950,309 | 8/1990 | Schulz | 48/197 R |
| 5,009,770 | 4/1991 | Miller et al. . | |
| 5,074,890 | 12/1991 | Schulz | 48/197 R |
| 5,179,129 | 1/1993 | Studer | 518/700 |
| 5,218,003 | 6/1993 | Lewnard et al. | 518/700 |
| 5,252,609 | 10/1993 | Pinto | 518/703 |
| 5,254,368 | 10/1993 | Kadlec et al. | 423/247 |
| 5,271,340 | 12/1993 | Whitney | 110/346 |
| 5,282,431 | 2/1994 | Kiss | 110/346 |
| 5,284,878 | 2/1994 | Studer et al. | 518/700 |
| 5,311,830 | 5/1994 | Kiss | 110/346 |
| 5,344,848 | 9/1994 | Steinberg et al. . | |
| 5,363,780 | 11/1994 | Whitney | 110/346 |
| 5,434,337 | 7/1995 | Kiss | 588/205 |
| 5,707,230 | 1/1998 | Kiss | 432/238 |
| 5,707,592 | 1/1998 | Someus . | |
| 5,711,924 | 1/1998 | Kiss | 423/240 R |
| 5,723,717 | 3/1998 | Kiss | 588/213 |
| 5,725,632 | 3/1998 | Kiss | 75/416 |
| 5,788,723 | 8/1998 | Kiss | 48/197 A |
| 5,865,023 | 2/1999 | Sorensen et al. | 60/39.02 |
| 6,084,139 | * 7/1999 | Giessen et al. | 585/240 |

* cited by examiner

Primary Examiner—Shailendra Kumar
Assistant Examiner—J. Parsa
(74) Attorney, Agent, or Firm—Troutman Sanders LLP; Gerald R. Boss, Esq.

(57) ABSTRACT

A process is provided for recycling heterogeneous waste including the initial step of subjecting the heterogeneous waste to pyrolysis to produce a synthesis gas stream comprising at least carbon monoxide and hydrogen and a molten pyrolysis product stream having a variable composition comprising at least a mineral material and a metallic material. The molten pyrolysis product stream is converted to a plurality of commercial grade solid materials. Likewise, the synthesis gas stream is also converted into at least one commercial grade chemical.

11 Claims, 3 Drawing Sheets

PROCESS FOR RECYCLING HETEROGENEOUS WASTE

BACKGROUND OF THE INVENTION

1. Field of Invention

This invention relates generally to a process for recycling mixed waste and more particularly to a process for maximizing the recycling of a heterogeneous hazardous waste stream having an uncontrolled, fluctuating content of carbon, metal, and minerals into separate, non-hazardous recycled components.

2. Description of Related Art

There is an ongoing need to dispose of hazardous waste generated by industries, most particularly the chemical industry. Hazardous waste is often either buried or burned, either of which can be costly processes, significantly increasing production costs for the products produced by the relevant industry. The costs for the disposal of hazardous waste typically, in part reflect the excise taxes and fees which must be paid to legally dispose of the waste. However, such hazardous waste disposal excise taxes and fees may be reduced or avoided totally by recycling the hazardous waste into commercial grade chemicals and materials, thereby decreasing the overall costs associated with disposal of the waste.

Gasification is one method of disposing of hazardous waste materials. Typically, the gasification process involves the step of "pyrolysis", which involves heating the waste material to a temperature wherein any water, hydrocarbons, and organic compounds are volatilized and the remaining mineral and metallic constituents are melted into a molten slag. After cooling and solidifying, the molten slag may either be disposed of or utilized in the production of steel. The volatilized hydrocarbons and organic compounds are generally disposed of by burning, and may in fact be consumed as an energy source. However, under current regulations, energy recovery of this sort from hazardous waste is still classified as disposal rather than recycling, thereby still incurring the full amount of taxes and fees associated with disposing of hazardous waste.

However, rather than burning the hydrocarbons and organic compounds, if the oxygen concentration present during the gasification process is controlled, it is possible to partially oxidize the vaporized hydrocarbons and organic compounds producing a "synthesis gas" which may be further processed. Synthesis gas typically includes substantial quantities of hydrogen ($H_2$) and carbon monoxide (CO), accompanied by lesser quantities of carbon dioxide ($CO_2$) and water ($H_2O$). Synthesis gas is a raw material suitable for the production of a number of commercial grade chemicals such as, for example and not limitation, ammonia, methanol, and dimethyl ether. Since the use of a synthesis gas to generate commercial products is classified as recycling under current regulations, the excise taxes and fees associated with hazardous waste disposal can be avoided by recycling the synthesis gas in this manner.

Methanol and dimethyl ether are both typically produced from synthesis gas on an industrial scale by a process involving the catalytic conversion of carbon monoxide and hydrogen. Methanol is produced from synthesis gas in the presence of a methanol synthesis catalyst by the reaction ($2H_2+CO \rightarrow CH_3OH$). Dimethyl ether is produced by the dehydration of methanol in the presence of a methanol dehydration catalyst by the reaction ($2CH_3OH \rightarrow H_2O + CH_3OCH_3$). Accordingly, it is often desirable to co-synthesize methanol and dimethyl ether in a reactor containing both a methanol synthesis catalyst and a methanol dehydration catalyst.

Conventional methods of forming methanol require careful balancing of the ratio of $H_2$ to CO present in the synthesis gas during the catalytic synthesis of methanol to approximately 2:1. An excess of carbon monoxide in the synthesis gas will result undesirable levels of carbon dioxide and carbon in the reactor, creating an exothermic event that overheats and ruins the catalyst. Conversely, an excess of hydrogen produces undesirable amounts of waste water during the methanol synthesis reaction which results in economically unfeasible treatment and purification costs. Accordingly, careful control of the composition and flow rate of the feedstock used to produce the synthesis gas is necessary for production of methanol or methanol and dimethyl ether.

For example, in one conventional process, coal is gasified using a strictly controlled feed rate of oxygen, in order to obtain a synthesis gas having a uniform composition and at a uniform rate. In another conventional process, methane is converted into a synthesis gas in a reaction with a precisely controlled amount of steam to produce a synthesis gas having a uniform composition at a uniform rate. In each of these cases, the feed material from which the synthesis gas is produced has a uniform composition, thereby allowing narrow control of the ratio of $H_2$ to CO in the synthesis gas.

Unfortunately, most industrial and hazardous wastes do not contain a uniform mixture of materials. Workers commonly throw a variety of undesirable items into the waste receptacles. Additionally, hazardous waste can contaminate the containers within which it is stored and transported, creating additional waste. Accordingly, the use of heterogeneous industrial and hazardous waste in a conventional gasification processes will result in a synthesis gas having a widely varying ratio of $H_2$ to CO. Thus, it has generally been thought that such heterogeneous industrial and hazardous wastes are unsuitable for use in the production of a synthesis gas suitable for the production of methanol and dimethyl ether.

Accordingly, it is an object of the present invention to provide a process for maximizing the recycling of heterogeneous waste, such as municipal solid waste, industrial waste and hazardous chemical waste into a plurality of commercial grade products and chemical compounds, thereby realizing economic gains from the resale of the commercial grade products avoiding excise taxes and fees associated with disposal of the waste.

Furthermore, it is an object of the present invention to provide a process for converting heterogeneous waste comprising a large number of miscellaneous, unidentified substances into a plurality of product streams having known compositions.

It is yet another object of the present invention to provide a system for converting heterogeneous carbon-containing waste into a synthesis gas having a desired composition suitable for the synthesis of methanol and/or dimethyl ether.

SUMMARY OF THE INVENTION

The above objectives are accomplished according to the present invention by providing a process for recycling heterogeneous waste including the initial step of subjecting the heterogeneous waste to pyrolysis to produce a synthesis gas stream comprising at least carbon monoxide and hydrogen and to produce a molten pyrolysis product stream having a variable composition comprising at least a mineral material and a metallic material. The molten pyrolysis product stream is converted to a plurality of commercial grade solid materials. Likewise, the synthesis gas stream is also converted into at least one commercial grade chemical.

BRIEF DESCRIPTION OF THE DRAWINGS

The construction and design to carry out the invention will hereinafter be described together with other features thereof. The invention will be more readily understood from a reading of the following specification and by reference to the accompanying drawings forming a part thereof, wherein an example of the invention is shown and wherein.

DETAILED DESCRIPTION OF PREFERRED EMBODIMENTS

Figure 1:
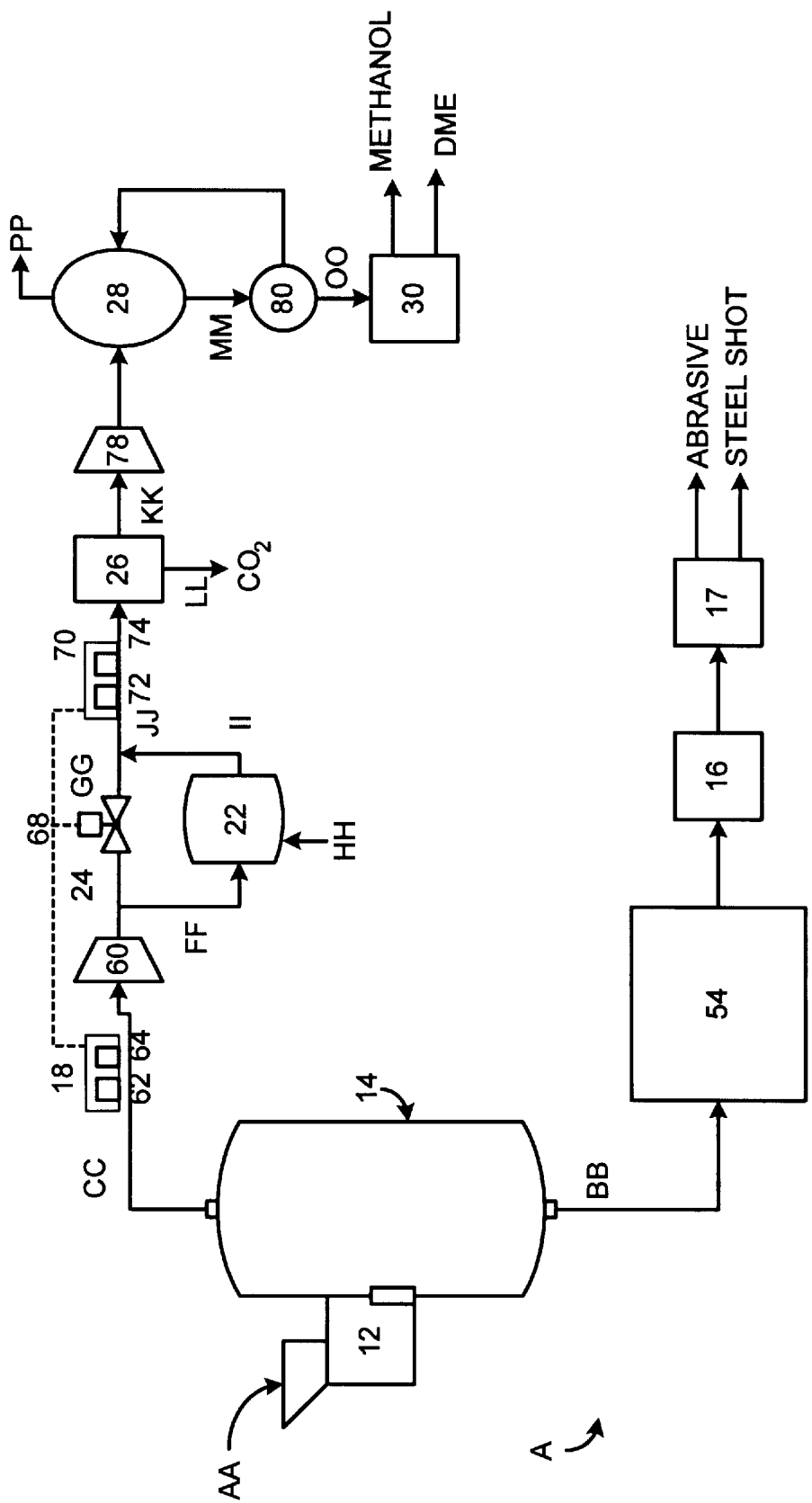
FIG. 1 is a block diagram illustrating the basic material flow pathways by which heterogeneous waste is recycled in accordance with a preferred embodiment of the present invention.

Referring now in more detail to the drawings, the invention will now be described in detail. As shown in FIG. 1, a heterogeneous waste recycling process A converts a heterogeneous mixture of waste material into a plurality of commercially useful solid products and chemical compounds. The term "heterogeneous waste material" as used herein refers to a non-homogeneous carbon-containing feedstock, the composition of which can vary widely over time as the result of variations in the composition of one or more of the feedstock components and/or variations in the relative amounts of the components in the feedstock. Solid and liquid carbon-containing waste materials containing large amounts of inorganic material are processable as heterogeneous feedstock according to the present invention. The carbon content of heterogeneous waste material AA will generally vary by more than ten weight percent over a given twenty-four hour period. However, in its preferred embodiment, the process of the present invention is capable of processing heterogeneous waste material AA having a carbon content varying by as much as thirty weight percent to fifty weight percent over a twenty-four hour period. Preferably, the net heating value of the heterogeneous feedstock is greater than approximately three thousand Btu/lb. Examples of the carbon-containing waste material that can be processed according to the present invention include municipal solid waste and hazardous industrial wastes such as oil-contaminated dirt, demolition debris, respirator masks, paint and contaminated rags.

As shown in FIG. 1, heterogeneous waste material AA is compressed in a waste compaction press 12 and fed into a gasifier 14 wherein it is pyrolytically converted into an undifferentiated molten slag stream BB and a raw synthesis gas stream CC having a variable ratio of $H_2$ to CO unsuitable for conversion to methanol by conventional methods. Undifferentiated molten slag stream BB is allowed to gravitationally separate to produce a molten mineral stream DD and a molten ferric alloy stream EE which are water quenched in a quenching chamber 16. Once quenched, molten mineral stream DD yields a vitreous material suitable for commercial use as an industrial abrasive and molten ferric alloy stream EE yields a ferric alloy suitable for commercial use in die casting metal production processes or as a shock blast material. The vitreous material and ferric allow material are magnetically separated by magnetic separator 17.

With respect to raw synthesis gas stream CC, the $H_2$:CO ratio is adjusted to render it suitable for the production of methanol or methanol and dimethyl ether. First, the $H_2$:CO ratio of raw $H_2$ synthesis gas stream CC is detected by synthesis gas composition sensor 18 and, in response to the sensed value thereof, a first portion FF of raw synthesis gas stream CC is directed via operation of a shift bypass valve 68 to shift reactor 22 while the remaining portion GG of raw synthesis gas stream CC flows through a shift reactor bypass line 24. Within shift reactor 22, first portion FF of raw synthesis gas stream CC is reacted with a selected amount of steam HH, both converting the CO therein to $CO_2$ and producing additional $H_2$ via the shift reaction (CO+$H_2O \rightarrow CO_2 + H_2$) to produce a shifted gas stream II predominantly comprising $CO_2$ and $H_2$. Shifted gas stream II is then mixed with remaining portion GG of raw synthesis gas stream CC to form a mixed synthesis gas stream JJ having a desired ratio of $H_2$ to CO and including substantial quantities of $CO_2$. Mixed synthesis gas stream JJ is directed to a $CO_2$ removal unit 26 wherein approximately greater than 98% of its $CO_2$ content is removed, producing a $CO_2$ depleted mixed synthesis gas stream KK and a $CO_2$ stream LL suitable for purification into commercial grade $CO_2$. $CO_2$ depleted mixed synthesis gas stream KK is then converted in a liquid phase catalyst reactor 28 to a useful product stream MM comprising methanol or a combination of methanol and dimethyl ether and subjected to separation and purification by methanol/DME recovery unit 30.

Alternatively, raw synthesis gas stream CC may also be utilized for the synthesis of ammonia according to the process disclosed in U.S. patent application Ser. No. 09/200, 150, entitled "Process for making Ammonia from Heterogeneous Feedstock," which is hereby incorporated by reference in its entirety. For conversion to ammonia, all of raw synthesis gas stream CC is directed through a shift reactor wherein its CO content is completely converted to $CO_2$. Subsequently, the $CO_2$ is removed and the resulting stream of purified hydrogen is reacted with nitrogen to produce commercially useful ammonia.

Figure 2:
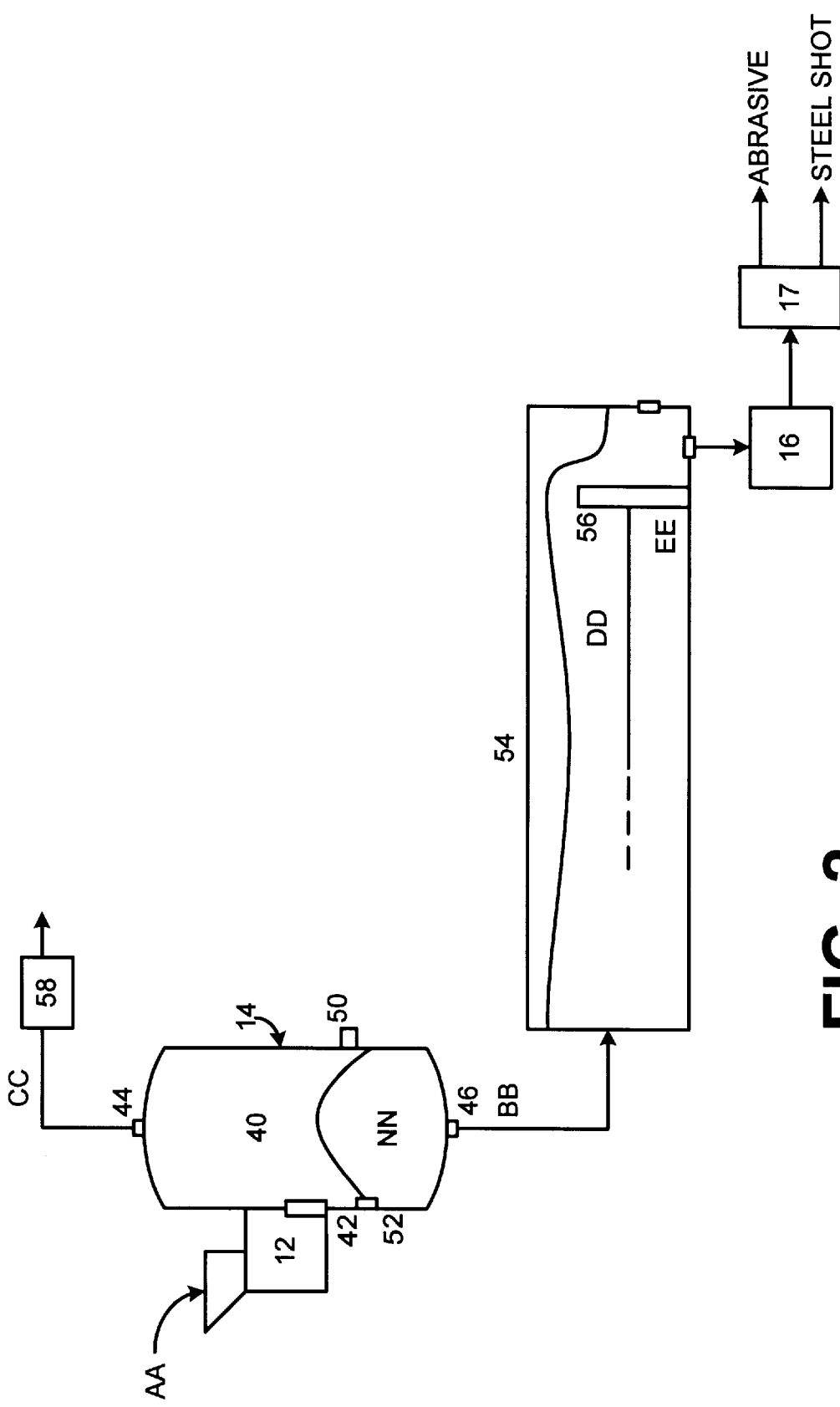
FIG. 2 is a schematic illustrating the basic operation of a gasifier for use in accordance with a preferred embodiment of the present invention.

As illustrated in FIG. 2, according to the process of the present invention, a quantity of a heterogeneous waste material AA is first compacted by a waste compaction press 12 mounted at the front of a gasifier 14 into plugs having approximately similar dimensions and mass. In addition to forming plugs of heterogeneous waste material AA, waste compaction press 12 also operates to force the compacted plugs of heterogeneous waste material AA into gasifier 14. In the preferred embodiment, waste compaction press 12 includes a conventional steel press rated at a maximum capacity of 320 psi, although any conventional press having sufficient capacity will suffice. Each compression cycle of waste compaction press 12 results in the introduction of a similarly sized plug of heterogeneous waste material into gasifier 14. Accordingly, the feed rate of heterogeneous waste material into gasifier 14 may be regulated simply by altering the cycle time of waste compaction press 12. In the preferred embodiment, waste compaction press 12 operates at a rate on the order of approximately 20 cycles per hour.

Gasifier 14 may be any conventional gasifier. Preferably, gasifier 14 is of the type disclosed in U.S. Pat. Nos. 5,788,723, 5,711,924, 5,282,431 and 5,707,230, which are incorporated herein by reference in their entireties. In the preferred embodiment, gasifier 14 includes an externally heated gasifier vessel 40 having a feed aperture 42 located along its midplane, a synthesis gas outlet 44 located at its upper end and a slag outlet 46 located at its bottom end. Feed aperture 42 serves as an open conduit to the atmosphere through which compacted plugs of heterogeneous waste material AA may be fed by press 12 into gasifier vessel 40. Accordingly, gasifier 14 operates at approximately atmospheric pressure. Upon injection into gasifier vessel 40, heterogeneous waste material AA is subjected to gasification by being heated to a pyrolysis temperature generally between 2000° C. and 3000° C., sufficient to volatilize any water, hydrocarbons, and other organic compounds entrained therein. The mixture of volatilized gases rises to the top of gasifier vessel 40 where it may undergo further reaction prior to exiting gasifier vessel 40 through synthesis gas outlet 44.

Meanwhile, the solid portions of heterogeneous waste material AA, including non-volatile organic compounds, metals, minerals and metallic oxides, fall to the bottom of gasifier vessel 40 forming a gasifier feed pile NN which is eventually melted into an undifferentiated molten slag stream BB. A selected amount of oxygen is injected into the lower portion of the gasifier vessel 40 to react with carbon and non-volatile organic compounds in gasifier feed pile CC, liberating additional CO, $CO_2$ and $H_2O$ into the gasifier vessel headspace. The remainder of undifferentiated molten slag stream BB flows through slag outlet 46 to an elongated separation chamber 54.

An excess carbon inventory should be maintained within the interior of gasifier vessel 40 in order to prevent an exothermic reaction of oxygen with the carbon monoxide in the pyrolysis gas, which can result in damage to gasifier vessel 40 and potentially an explosive exothermic event. In the preferred embodiment, this carbon excess is ensured by monitoring the height of gasifier feed pile NN and adjusting feed rate of heterogeneous waste material AA to maintain gasifier feed pile NN above a minimum height which assures that an excess carbon inventory is present within oxygen to gasifier vessel 40. The height of gasifier feed pile NN is preferably sensed by a gamma ray attenuation detector 50, which measures the attenuation of gamma radiation emitted from a source 52 having a known intensity diminution as it passes through gasifier feed pile NN.

In the preferred embodiment, undifferentiated molten slag stream BB flows through slag outlet 46 to separation chamber 54 wherein the components of the slag gravitationally separate into a layer of mineral material floating on top of a layer of molten ferric alloy. Separation chamber 54 includes weir 56 over which the upper mineral layer and lower ferric alloy layer alternatively flow. The molten mineral stream and molten ferric alloy stream are then quenched in a quenching chamber 16, which includes a 30 inch diameter tube through which the molten material falls while being sprayed with jets of water which breakup the molten material into small particles while quenching it. The quenched particles then fall to the bottom of quenching chamber 16.

Upon quenching. the molten mineral stream DD, solidifies into particles of a vitreous material having a specific gravity of approximately 2.25. The vitreous material is generally useful as an airblast abrasive when pulverized to an appropriate size. This is a particularly useful commercial product since a market exists for approximately one million tons of such airblast abrasive per year and the current primary sources for this material, coal fired power plants, are currently being phased out. Upon quenching the molten ferric alloy stream EE, solidifies into particles of a steel shot, wherein the majority of environmental metals are alloyed into the steel. This steel shot is generally suitable for use as feedstock into die casting metal production processes or, after tempering, as a shock blast material.

Following quenching, the mixed particles of vitreous material and steel shot are transferred by a bucket elevator from the bottom of quenching chamber 16 to a magnetic separator 17. Magnetic separator 17 operates to separate the particles into a steel shot product stream comprising particles of the ferrous alloy and a vitreous stream comprising particles of the vitreous material.

The temperature of the pyrolysis gas in gasifier vessel 40 is preferably maintained at a value of at least 2100 degrees C., sufficient to crack entrained hydrocarbons to form a carbon soot and $H_2$ and to drive the endothermic reactions necessary for the production of a synthesis gas rich in $H_2$ and CO. Steam produced by the heat of fusion liberated by the quench reactions of the mineral and ferric slag streams flows as a counter current back into the gasifier vessel 40 allowing for the conversion of carbon from soot and entrained hydrocarbons to CO in the pyrolysis gas via the endothermic reaction ($C+H_2O \rightarrow CO+H_2$), further increasing the concentrations of CO and $H_2$ in the synthesis gas. Additionally, a substantial amount of the carbon and $CO_2$ in the pyrolysis gas is also converted to CO via the Boudard reaction ($CO_2+C \rightarrow 2CO$).

The temperature and gas flow rate of gasifier vessel 40 are controllable to desired values as follows. The temperature of the pyrolysis gas in the upper portion of gasifier vessel 40 is controllable by adjusting the rate at which oxygen is injected into the upper portion of gasifier vessel 40 to exothermically react with carbon, CO and $H_2$ therein. Accordingly, temperature of the pyrolysis gas is increased by increasing the amount of oxygen injected into the upper portion of gasifier vessel 40 and decreased by decreasing amount of oxygen injected into the upper portion of gasifier vessel 40. In the preferred embodiment, a small amount of methane may also be injected with the oxygen into the upper portion of gasifier vessel 40 to avoid quenching the pyrolysis gas prior to injection of the oxygen.

The flow rate of gas exiting gasifier vessel 40 is controllable by altering the rate at which oxygen is injected into the bottom portion of gasifier vessel 40. To increase the flow rate of gas leaving gasifier vessel 14, the flow rate of oxygen into the bottom portion of gasifier vessel 40 is increased, driving the exothermic gasification of carbon and non-volatile organic constituents of gasifier feed pile NN into CO, $H_2$ and $CO_2$, thereby increasing the gas flow rate leaving gasifier vessel 40. Increasing the flow of oxygen into the bottom portion of gasifier vessel 40 may also necessitate increasing the feed rate of heterogeneous waste material AA into gasifier vessel 40 to compensate for the additional consumption of material from gasifier feed pile NN. Of course, increasing the feed rate of heterogeneous waste material AA into gasifier vessel 40 will increase the amount of steam flowing back into gasifier vessel from quenching the resulting increased flows of molten mineral material DD and molten ferric alloy EE, which may also serve to increase the gas flow rate since the steam may react with carbon components in gasifier feed pile NN to produce CO, $H_2$ and $CO_2$. Conversely, to reduce the gas flow rate exiting gasifier vessel 40, the oxygen injection rate into the bottom portion of gasifier vessel 40 is simply decreased.

The raw synthesis gas CC exiting gasifier vessel 40 through synthesis gas outlet 44 has a variable composition, typically comprising at least carbon monoxide (CO), carbon dioxide ($CO_2$) and hydrogen ($H_2$). The raw synthesis gas CC preferably has a composition of approximately twenty volume percent to approximately fifty-four volume percent of both CO and $H_2$, with the amount of CO exceeding the amount of $H_2$. Additionally, raw synthesis gas CC will usually include approximately twenty volume percent to thirty volume percent $CO_2$. The raw synthesis gas CC exiting gasifier vessel 40 also may include approximately 1% carbon soot and trace amounts of sulfur, halogens, and volatile metals.

Next, the raw synthesis gas CC is directed to gas treatment system 58 wherein it is quenched with water at a 25:1 water/gas ratio. The quench reaction occurs through a complex reversing flow which shock cools raw synthesis gas stream CC to approximately 156° F. The use of high speed shock cooling ensures that there is no time for the de novo synthesis of dioxins and dibenzofurans during the quench. In addition to cooling raw synthesis gas stream CC, the quench water serves to remove the majority of contaminating soot from raw synthesis gas stream CC. The quench water also absorbs halogens and the majority of contaminating sulfur. This lowers the pH of the quench water to approximately two, increasing the quench water's solubility for metals and thereby allowing it to also dissolve the majority of contaminating metals from raw synthesis gas stream CC. In the preferred embodiment, the quench water is subjected to a series of conventional water filtration and precipitation treatment steps, as would be known to one of ordinary skill in the art, wherein the majority of these contaminants are separated and recycled.

Following the water quench, raw synthesis gas stream CC preferably undergoes a series of wash steps to further remove contaminants. First, raw synthesis gas stream CC is subjected to an alkaline wash to remove any acid radicals. Next, raw synthesis gas stream CC is subjected to a glycerin wash to remove hydrophobic carbon particles. Next, raw synthesis gas stream CC is subjected to a sulfur chelating wash, using a sulfur chelating agent which removes $H_2S$, COS and other contaminating sulfur compounds. Next, raw synthesis gas stream CC is subjected to a chilled water wash at approximately 45° F. to condense mercury. Finally, raw synthesis gas stream CC is reheated to approximately 113° F. and passed through an activated carbon filter for a final polish. In this presently preferred system, following the wash steps, raw synthesis gas stream CC is extremely pure, having approximately 50 parts per billion sulfur, 50 parts per billion halogens and 10 parts per billion of heavy metals.

As previously mentioned, the stoichiometric ratio of $H_2$ to CO required for the synthesis of methanol is 2:1. Conventional processes for methanol synthesis are run in a reactor at an excess of $H_2$, for example having $H_2$:CO ratios of 2.1–2.2:1, in order to avoid overheating the catalyst or sooting up the catalyst through the deposition of carbon upon the methanol synthesis catalyst. Unfortunately, the excess hydrogen in the process results in the production of greater amounts of waste water from the reaction. As this waste water contains detectable percentages of methanol and other byproducts, it must be treated prior to release. Therefore, minimization of the amount of waste water produced during the reaction would be desirable.

In the present process, therefore, the synthesis gas fed into the methanol synthesis reaction is desired to have at most no more than the stoichiometric amount of hydrogen, and preferably less than the stoichiometric amount of hydrogen, thereby minimizing the generation of waste water. For example, in the preferred embodiment, the ratio of $H_2$:CO of the synthesis gas fed to the reactor should preferably be CO rich, between 1.95–2.0:1 inclusive, for the synthesis of methanol. Accordingly, it is necessary to adjust the ratio of $H_2$:CO of the synthesis gas to the desired range.

As shown in FIG. 1, after washing, the ratio of $H_2$:CO in raw synthesis gas stream CC is sensed by a raw synthesis gas composition sensor 18. In the preferred embodiment, raw synthesis gas composition sensor 18 includes an infrared spectrophotometric sensor 62 for sensing the amounts of CO and $CO_2$ in raw synthesis gas stream CC and a specific heat sensor 64 for sensing the amount of $H_2$ in raw synthesis gas stream CC. Infrared spectrophotometric sensor 62 operates generally by measuring the absorption, at wavelengths specific for CO and $CO_2$ respectively, of a beam of infrared light passing through raw synthesis gas CC. Specific heat sensor 64 is an online gas analyzer which operates by diverting a sample flow from raw synthesis gas stream CC, heating the sample stream to a known temperature, and then adding a standard energy input, such as from a heating filament, and measuring the change in temperature of the sample stream to determine the specific heat of raw synthesis gas stream CC. Since the specific heat of $H_2$ is approximately an order of magnitude higher than the specific heats of CO and $CO_2$ respectively, the specific heat of raw synthesis gas stream CC directly relates to its approximate hydrogen content.

Raw synthesis gas stream CC is compressed to a pressure of, for example, about 160 psi or more, using raw synthesis gas compressor 60 in order to drive it through subsequent process steps. The ratio of $H_2$:CO of the raw synthesis gas CC is adjusted by directing a first portion FF of raw synthesis gas stream CC into a shift reactor 22, while the remaining portion GG of raw synthesis gas stream CC flows through a shift reactor bypass line 24. The percentage of raw synthesis gas stream CC diverted into shift reactor 22 is controlled by regulating the position of shift bypass valve 68 in response to the sensed composition of raw synthesis gas stream CC. In the preferred embodiment, the percentage of raw synthesis gas stream CC to be diverted is controlled in response to the measured ratio of $H_2$:CO of raw synthesis gas stream CC.

Within shift reactor 22, a selected amount of water HH, in the form of steam, is mixed with first portion FF of raw synthesis gas stream CC. The steam and CO in the first portion FF of raw synthesis gas stream CC react via the shift reaction ($CO+H_2O \rightarrow CO_2+H_2$) to produce a shifted gas stream II containing primarily $CO_2$ and $H_2$. In the preferred embodiment, substantially all (approximately ninety eight percent) of the CO content of first portion FF of raw synthesis gas stream CC is converted into $CO_2$. The amount of steam injected into shift reactor 22 is selected to approximately correspond to the CO content of first portion FF of raw synthesis gas stream CC based upon the sensed $H_2$:CO ratio of raw synthesis gas stream CC, thereby maximizing conversion of CO to $CO_2$ and minimizing the water content of shifted gas stream II.

In a simplified exemplary embodiment, the percentage of raw synthesis gas stream CC which must be diverted into shift reactor 22 is generally determined under the relationship $x=(2y-z)/3y$, wherein x is the percent of raw synthesis gas stream CC to be shifted, y is the initial percentage of raw synthesis gas stream CC which is CO and z is the initial percentage of raw synthesis gas stream CC which is $H_2$. This relationship takes into account both the decrease in CO and the increase in $H_2$ which result from the shift reaction. For example, to shift a raw synthesis gas stream CC having a composition of 40 percent CO, 30 percent $H_2$, and 30 percent $CO_2$ to a desired $H_2$:CO ratio of 2:1 we find that x=(2(0.4)−0.3)/3(0.4) which simplifies to x=0.4166 or 41.66%. Therefore, to shift a raw synthesis gas stream CC having a composition of 40 percent CO, 30 percent $H_2$, and 30 percent $CO_2$ to a desired $H_2$:CO ratio of 2:1, approximately 41.66% of the flow of raw synthesis gas stream CC must be directed to shift reactor 22.

Shifted gas stream II is then mixed with remaining portion GG of raw synthesis gas stream CC to form a mixed synthesis gas stream JJ having the approximate desired $H_2$:CO ratio (approximately 1.95 to 2.0) and including substantial quantities of $CO_2$. The actual ratio of $H_2$:CO in mixed synthesis gas stream JJ is sensed by mixed synthesis gas composition sensor 70 and may be used as a trim signal to make minor adjustments to the bypass flow rate and steam flow rate to shift reactor 22. Mixed synthesis gas composition sensor 70 may be any means of sensing the composition a raw synthesis gas stream CC which would be known to one of ordinary skill in the art. However, in the preferred embodiment, mixed synthesis gas composition sensor 70 includes an infrared spectrophotometric sensor 72 and a specific heat sensor 74 similar to those of raw synthesis gas composition sensor 18.

In the preferred embodiment, mixed synthesis gas stream JJ is subsequently directed to a $CO_2$ removal unit 26 wherein approximately greater than 98% of its $CO_2$ content is removed, producing a $CO_2$ depleted mixed synthesis gas stream KK having the desired ratio of $H_2$:CO and a $CO_2$ stream LL suitable for purification into commercial grade $CO_2$. In the preferred embodiment, $CO_2$ removal unit 26 operates by passing mixed synthesis gas stream JJ through an aqueous solution of an amine base which capable of binding the carbonic acid form of $CO_2$. Of course, one of ordinary skill in the art will recognize that $CO_2$ removal unit 26 may be selected from a number of other conventional $CO_2$ removal systems. Also, in alternative embodiments, the carbon dioxide from the shift reaction can be left in the synthesis gas and removed following the formation of the methanol and/or dimethyl ether, if desired, without adversely affecting the reaction except by increasing the amount of waste water in the product.

The $CO_2$ depleted mixed synthesis gas stream KK is next preferably compressed to approximately 950 psia by mixed synthesis gas compressor 78 and directed into liquid phase catalyst reactor 28 for conversion into a useful product stream MM comprising either methanol or a mixture of methanol and dimethyl ether. Liquid phase catalyst reactor 28 is preferably of the type developed by Air Products and Chemicals, Inc., as disclosed in U.S. Pat. Nos. 5,179,129, 5,218,003, 4,910,227, 4,766,154, 5,284,878 and 4,628,066 which are incorporated herein in their entireties by reference. As described in these references, the liquid phase reactor may be selectively operated at from approximately 750 to 1500 psia to produce a product stream MM comprising either methanol or a mixture of methanol and dimethyl ether from a CO rich synthesis gas stream such as $CO_2$ depleted mixed synthesis gas stream KK. Methanol is produced from synthesis gas in the presence of a methanol synthesis catalyst by the reaction ($2H_2+CO\rightarrow CH_3OH$). Dimethyl ether is produced by the dehydration of methanol in the presence of a methanol dehydration catalyst by the reaction ($2CH_3OH\rightarrow H_2O+CH_3OCH_3$)

In the preferred embodiment, liquid phase catalyst reactor 28 operates at a temperature of about 200° C. to 250° C. and a pressure of about 950 psia. Liquid phase catalyst reactor 28 includes at least one methanol synthesis catalyst, such as a conventional copper-containing catalyst, suspended in an inert liquid. The liquid for the liquid phase reactor may be any suitable liquid described in the foregoing references incorporated herein by reference, including, for example, hydrocarbons, alcohols, ethers, polyethers, etc. For producing both methanol and dimethyl ether, the liquid phase reactor should contain not only the methanol synthesis catalyst, but should also contain a methanol dehydration catalyst. The methanol dehydration catalyst can be any conventional catalyst known in the art for this purpose including, for example, alumina, silica-alumina, zeolites, solid acids such as boric acid, solid acid ion exchange resins such as perfluorinated sulfonic acid, etc.

Since the $CO_2$ depleted mixed synthesis gas stream KK has a $H_2$:CO ratio slightly lower than the stoichiometric value of 2.0 for the methanol synthesis reaction, the production of waste water in liquid phase catalyst reactor 28 is minimized. In fact, compared to conventional gas phase methanol synthesis processes that operate on the hydrogen rich side of the stoichiometric value, the amount of waste water produced in the present process is reduced on the order of ten times or more.

Liquid phase catalyst reactor 28 is effective to convert approximately 40% of the CO and $H_2$ in $CO_2$ depleted mixed synthesis gas stream KK to methanol per pass through liquid phase catalyst reactor 28. Accordingly, product stream MM also includes the remaining unreacted 60% of the initial CO and $H_2$ from $CO_2$ depleted mixed synthesis gas stream KK. Therefore, product stream MM is next directed to condenser 80 wherein the products methanol and dimethyl ether and any contaminating water and $CO_2$ are condensed to form a liquid product stream OO. The remainder of product stream MM, comprising mostly CO and $H_2$ is then recycled back into liquid phase catalyst reactor 28 for subsequent reaction into methanol or methanol and dimethyl ether. By continually recycling CO and $H_2$ from product stream MM, near complete conversion of the CO and $H_2$ to methanol or methanol and dimethyl ether may be achieved. However, small waste gas stream PP comprising approximately two percent of the flow of product stream MM is removed from liquid phase catalyst reactor 28 via a purge line to prevent the buildup of any contaminating non-reactive gases therein.

Figure 3:
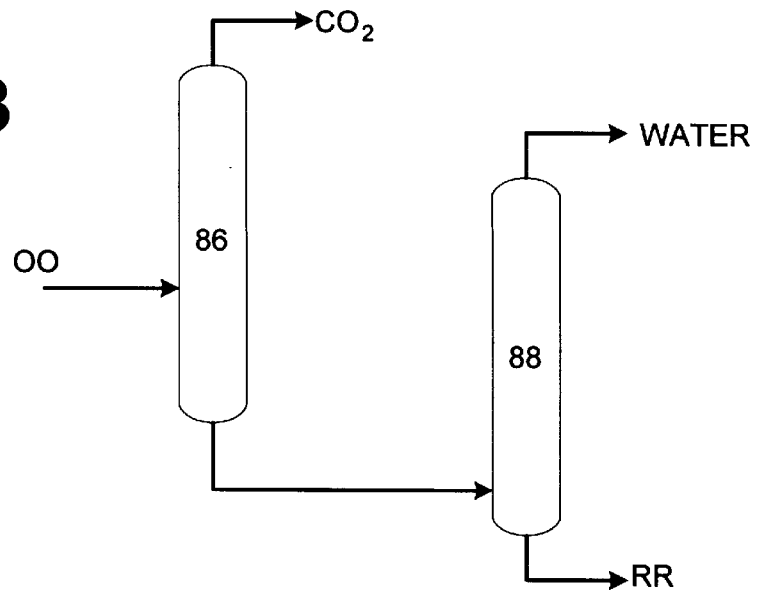
FIG. 3 is a block diagram illustrating a methanol purification process in accordance with a preferred embodiment of the present invention.

Liquid product stream OO is fed to methanol/DME recovery unit 30 to separate the methanol and dimethyl ether products from carbon dioxide and water. As seen in FIG. 3, when liquid phase catalyst reactor 28 is operating in methanol only mode, methanol/DME recovery unit 30 includes a first distillation column 86 through which liquid product stream OO is passed for separating out any carbon dioxide which may be dissolved therein. Liquid product stream OO then passes through a second distillation column 88 which separates out any contaminating water, producing a high purity methanol stream RR.

Figure 4:
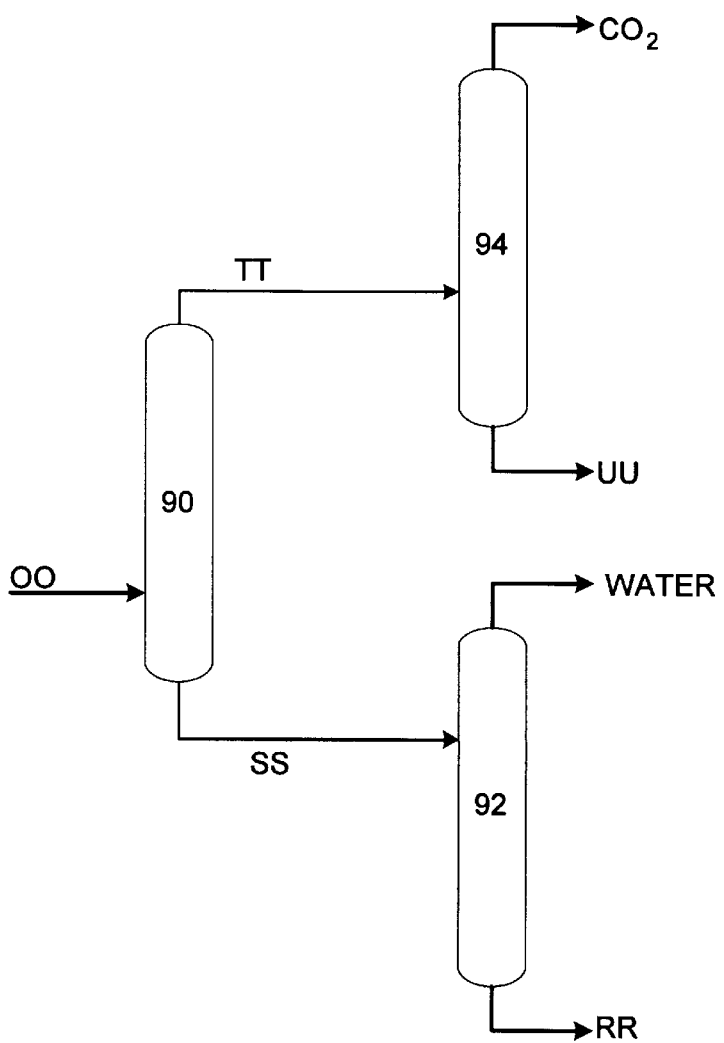
FIG. 4 is a block diagram illustrating a methanol and dimethyl ether purification process in accordance with a preferred embodiment of the present invention.

As seen in FIG. 4, when liquid phase catalyst reactor 28 is operating in methanol/dimethyl ether mode, methanol/DME recovery unit 30 includes a first distillation column 90 through which liquid product stream OO is passed to separate it into a methanol/water stream SS and a dimethyl ether/carbon dioxide stream TT. Methanol/water stream SS is then passed through a second distillation column 92 which separates out any contaminating water to produce high purity methanol stream RR. Dimethyl ether/carbon dioxide stream TT is passed through a third distillation column 94 which separates out any contaminating carbon dioxide to produce high purity dimethyl ether stream UU.

Thus, it may be seen, that an advantageous process to maximize the recycling of heterogeneous waste is provided according to the present invention. The recycling of heterogeneous waste may be maximized by pyrolytically converting it into a plurality of useful solid components and a synthesis gas having a variable composition, including CO and $H_2$. By removing a portion of CO from the synthesis gas, the composition of the synthesis gas may be adjusted to render it suitable for the production of methanol and/or dimethyl ether. Furthermore, by using a liquid catalyst reactor, the production of methanol and/or dimethyl ether may be accomplished while minimizing the generation of waste water. Accordingly, by utilizing the present invention, a heterogeneous waste material having a variable and unknown composition is convertible into a plurality of useful material streams having known compositions, including a ferric alloy stream, a vitreous material stream, a methanol stream, a dimethyl ether stream, a carbon dioxide stream, and miscellaneous streams containing sulfur and salts, thereby realizing economic gains from the resale of the commercial grade products in addition to receiving excise tax and fee benefits.

It thus will be appreciated that the objects of this invention have been fully and effectively accomplished. It will be realized, however, that the foregoing preferred specific embodiment has been shown and described for the purpose of this invention and is subject to change without departure from such principles. Therefore, this invention includes all modifications encompassed within the spirit and scope of the following claims.

What is claimed is:

1. A process for recycling heterogeneous waste comprising the steps of:
    subjecting the heterogeneous waste to pyrolysis to produce a synthesis gas stream comprising carbon monoxide and hydrogen and a molten pyrolysis product stream comprising at least a mineral material and a metallic material;
    converting said molten pyrolysis product stream to a plurality of useful solid materials by:
        allowing said molten pyrolysis product stream to gravitationally segregate into metallic portion and a mineral portion;
        quenching said metallic portion of said molten pyrolysis product stream to form a ferric alloy;
        quenching said mineral portion of said molten pyrolysis product stream to form a vitreous material; and
    converting said gaseous pyrolysis product stream into at least one useful chemical by:
        sensing the ratio of hydrogen to carbon monoxide of said synthesis gas stream;
        in response to said sensed ratio of hydrogen to carbon monoxide of said synthesis gas stream, separating said synthesis gas stream into a first stream and a second stream;
        introducing said first stream into a shift reactor, said shift reactor increasing the ratio of hydrogen to carbon monoxide of said first stream to produce a shifted gas stream;
        mixing said shifted gas stream with said second stream to produce a mixed synthesis gas stream, said mixed synthesis gas stream having a desired ratio of hydrogen to carbon monoxide; and
        converting said mixed synthesis gas to at least one commercial grade chemical selected from the group consisting of ammonia, methanol or dimethyl ether.

2. The process of claim 1 wherein said desired ratio of hydrogen to carbon monoxide is in the range of approximately 1.95 to approximately 2.0 molecules of hydrogen per molecule of carbon monoxide.

3. The process of claim 1, wherein said heterogeneous waste has a net heating value of at least 3000 BTU/lb.

4. The process of claim 1, wherein said pyrolysis step is conducted in a gasifier and wherein an excess carbon inventory is maintained in said gasifer during said pyrolysis step.

5. The process of claim 1, wherein said commercial grade chemical is produced by reacting said synthesis stream with a catalyst in a liquid phase reactor.

6. The process of claim 1, wherein said commercial grade chemical is methanol and said methanol is produced in a liquid phase reactor including a methanol synthesis catalyst.

7. The process of claim 1, wherein said commercial grade chemical is dimethyl ether and said dimethyl ether is produced in a liquid phase reactor including a methanol synthesis catalyst and a methanol dehydration catalyst.

8. The process of claim 1, further including the step of recovering the commercial grade chemical.

9. The process of claim 8, wherein said recovering step includes the step of recovering the commercial grade chemical from a distillation column which separates the commercial grade chemical from water.

10. The process of claim 9, further including the step of condensing said commercial grade chemical from the gas exiting said liquid phase reactor and wherein unreacted synthesis gas components are recycled back to said liquid phase reactor.

11. The process of claim 1, wherein said mixed synthesis gas stream further includes carbon dioxide and said process further includes the removal a portion of said carbon dioxide from said synthesis gas stream.

* * * * *